(12) United States Patent
Xu et al.

(10) Patent No.: US 7,573,975 B2
(45) Date of Patent: Aug. 11, 2009

(54) METHOD AND DEVICE FOR SHAPING AN ENERGY INPUT BEAM

(75) Inventors: Yuan Xu, Eugene, OR (US); Oleg Tischenko, München (DE); Christoph Hoeschen, Hebertshausen (DE)

(73) Assignees: State of Oregon Acting By and Through the State Board of Higher Education on Behalf of the University of Oregon, Eugene, OR (US); Helmholtz Zentrum Munchen Deutsches Forschungszentrum fur Gesundheit (GmbH), Neuherberg (DE)

(*) Notice: Subject to any disclaimer, the term of this patent is extended or adjusted under 35 U.S.C. 154(b) by 0 days.

(21) Appl. No.: 11/794,557

(22) PCT Filed: Dec. 21, 2005

(86) PCT No.: PCT/EP2005/013802

§ 371 (c)(1),
(2), (4) Date: Jan. 17, 2008

(87) PCT Pub. No.: WO2006/069709

PCT Pub. Date: Jul. 6, 2006

(65) Prior Publication Data

US 2008/0165917 A1 Jul. 10, 2008

Related U.S. Application Data

(60) Provisional application No. 60/640,426, filed on Dec. 30, 2004.

(30) Foreign Application Priority Data

Dec. 30, 2004 (EP) .................... 04031043
May 23, 2005 (EP) .................... 0501136

(51) Int. Cl.
*A61B 6/00* (2006.01)
(52) U.S. Cl. .................... 378/16; 378/149
(58) Field of Classification Search ........... 378/4–20, 378/149

See application file for complete search history.

(56) References Cited

U.S. PATENT DOCUMENTS 4,304,999 A * 12/1981 Richey et al. ............ 378/4
4,315,157 A 2/1982 Barnes et al.
6,343,110 B1 1/2002 Li

OTHER PUBLICATIONS

Bortfeld T. et al., "Fast and exact 2D image reconstruction by means of Chebyshev decomposition and backprojection," Physics in Medicine and Biology 44:1105-1120 (Apr. 1999).
Hanson and Wecksung, "Local basis-function approach to computed tomography," Appl. Opt. 24:4028-4039 (Dec. 1985).

* cited by examiner

*Primary Examiner*—Courtney Thomas
(74) *Attorney, Agent, or Firm*—Klarquist Sparkman, LLP (57) ABSTRACT

An irradiation method, in particular for imaging a region of investigation (2) of an object (1), comprises generating at least one energy input beam (3) with at least one energy input beam source (210), wherein the at least one energy input beam (3) comprises a plurality of individual energy input beam components (3.1, 3.2, 3.3, . . . ), and irradiating the region of investigation (2) with the at least one energy input beam (3) along a plurality of projection directions, wherein the energy input beam components (3.1, 3.2, 3.3, . . . ) are formed with at least one beam mask (211) made of an energy input shielding material with through holes. Furthermore, imaging methods and devices for irradiating or imaging the object are described.

30 Claims, 4 Drawing Sheets

METHOD AND DEVICE FOR SHAPING AN ENERGY INPUT BEAM

CROSS REFERENCE TO RELATED APPLICATIONS

This is the U.S. National Stage of International Application No. PCT/EP2005/013802 filed Dec. 21, 2005, which was published in English under PCT Article 21(2), which in turn claims the benefit of European Application No. 05011136.8, filed May 23, 2005, European Application No. 04031043.5, filed Dec. 30, 2004, and U.S. Provisional Application No. 60/640,426, filed Dec. 30, 2004. These applications are incorporated herein by reference.

ACKNOWLEDGEMENT OF GOVERNMENT SUPPORT

This invention was made with Government support under Grant No. DMS-02011669 awarded by the National Science Foundation, U.S.A. The Government of the United States of America has certain rights in the invention.

TECHNICAL FIELD

The present invention relates to a method for shaping an energy input beam for imaging purposes, in particular to an irradiation method for imaging a region of investigation of an object with at least one energy input beam. Furthermore, the present invention relates to a method and devices for imaging the region of investigation on the basis of the irradiation method, in particular for imaging tomography.

TECHNICAL BACKGROUND

Figure 9:
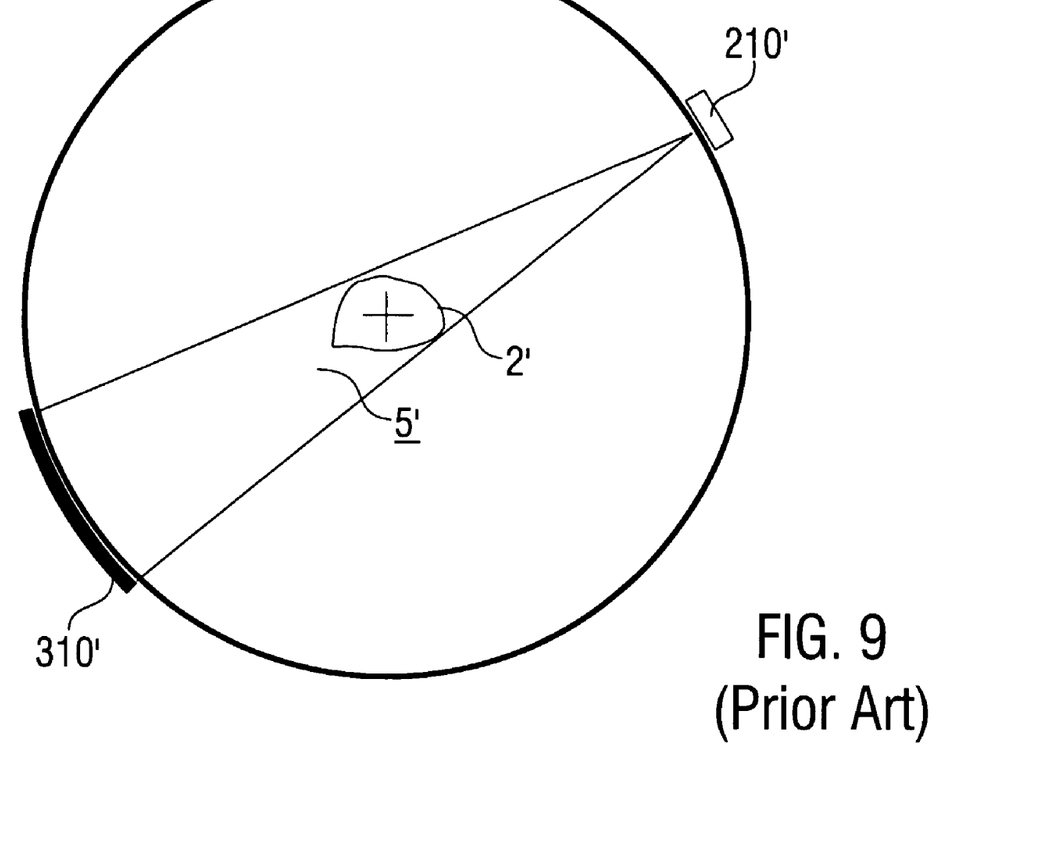
FIG. 9 a schematic illustration of directing a conventional fan beam through a region of investigation (prior art).

The non-destructive investigation of samples is an important object in various technical fields like material sciences, medical examinations, archaeology, construction technique, techniques concerning security matters etc. One approach for obtaining an image of a sample e.g. by computer tomography (CT) is based on an irradiation trough a object plane from different projection directions with X-rays, followed by a reconstruction of the object plane on the basis of attenuation data measured at different directions. The irradiation of a region of investigation 2' with a conventional fan beam 5' created by an X-ray source 210' is schematically illustrated in FIG. 9. The fan beam 5' comprises a continuous distribution of electro-magnetic fields shaped according to an emission characteristic of the X-ray source 210'. The entirety of the attenuation data measured with a detector 310' can be described in terms of so-called Radon data in a Radon space.

The most relevant conventional reconstruction methods known today can be summarized as methods based on the iterative reconstruction or those based on the so-called filtered back-projection. The iterative reconstruction methods have essential disadvantages in terms of extremely long calculation times. On the other hand, the filtered back-projection method has a general disadvantage as an interpolation step included in the reconstruction results in errors and artifacts which have a tendency even to increase with increasing space frequency. Another problem of the filtered back-projection method is related to the discretization of the Radon data from which the image data have to be reconstructed. To get an optimal filtered back-projection reconstruction it would be necessary to exactly match the projected irradiation rays with detector elements of a detector. This is in general not the case. For this reason, uncertainties or smoothing effects from the reconstruction of Radon data by means of filtered back-projection algorithms are introduced.

T. Bortfeld et al. have described a so-called Chebyshev domain filtered back projection (CD-FBP) algorithm for the reconstruction of two-dimensional images from a plurality of projections along the projection directions ("Phys. Med. Biol.", Vol. 44, 1999, p. 1105-1120). With this CD-FBP algorithm, the projections are represented as decompositions, which are subjected to the above filtered back-projection reconstruction. The projections are measured e.g. with a fan beam geometry, wherein attenuation values according to single projection lines with even angular intervals relative to each other are measured. The single projection lines measured with different projection directions of the fan beam can be resorted for providing parallel projections to be used for the image reconstruction. The CD-FBP algorithm has not yielded a practical implementation. The algorithm assumes an ideal fan beam geometry, which is not available in practice. Therefore, the T. Bortfeld et al. algorithm requires an interpolation step like the conventional filtered back-projection. Furthermore, as the CD-FBP algorithm is inherently discrete, there is a lack of adaptation to the continuous radiation characteristic of conventional radiation sources. Finally, the CD-FBP algorithm has an essential disadvantage in terms of artifacts occurring in the reconstructed images.

The above disadvantages are associated not only with the conventional CT imaging, but also with all available reconstruction methods related to Radon data.

OBJECTIVE OF THE INVENTION

The objective of the invention is to provide improved methods for irradiating an object, which avoid the disadvantages of the above conventional techniques and which in particular can be used for improved imaging. In particular, the objective of the invention is to provide an irradiation method with an improved adaptation of a radiation source to the image reconstruction algorithm to be used. Furthermore, the objective of the invention is to provide an improved imaging device, which is capable of improved imaging a region of investigation in particular with reduced artifacts.

The above objectives are achieved with methods or devices comprising the features of patent claims 1, 14 and 26. Advantageous embodiments and applications of the invention are defined in the dependent claims.

SUMMARY OF THE INVENTION

According to a first general aspect of the invention, an irradiation method is provided wherein at least one energy input beam is shaped with at least one beam mask for providing a plurality of individual energy input beam components. The beam mask is made of an energy input shielding material with through holes providing the number of beam components and forming the distribution thereof. The individual energy input beam components formed by the shielding effect of the mask (lattice) are directed through an object along a plurality of projection lines for imaging a region of investigation in the object.

The energy input beam with a primary continuous radiation characteristic is generated as a fan beam or a cone beam by using an energy input beam source. Subsequently, the energy input beam is shaped with the beam mask. The essential advantage of shaping the energy input beam for forming the energy input beam components is given by the fact that a discrete irradiation characteristic is provided inherently. The irradiation characteristic can be adapted to an image reconstruction algorithm used for imaging the region of investigation. This adaptation is obtained simply by selecting a predetermined beam mask and/or adjusting the beam mask relative to the energy input beam source. The beam mask has a predetermined geometry with a fixed distribution and fixed size(s) of the through holes. Furthermore, the energy input (e.g. dose) can be reduced essentially.

The fan or cone beams are adjusted such that the projection directions are set in at least one common plane crossing the region of investigation or, alternatively, in varying in-lined planes crossing the region of investigation for obtaining helical projection data.

The term "region of investigation" (ROI) used herein generally refers to an object under investigation or a part thereof. The ROI can be described as a 2- or 3-dimensional entity. The term "projection direction" used herein generally refers to the linear course of an energy input through the ROI. The projection direction can be defined by angles relative to a coordinate system used. If fan or cone beams are considered, the term "projection direction" indicates the orientation of a central (or: main) beam component in the fan or cone beam.

According to a preferred embodiment of the invention, the energy input beam source is movable relative to the object, wherein the beam mask and the energy input beam source are connected with each other. In this case, the beam mask is called source mask. The projection directions can be selected by moving the energy input beam source and the source mask relative to the region of investigation. Particularly preferred is an embodiment, wherein the projection directions are set subsequently by rotating the energy input beam source with the beam mask around the object.

According to an alternative embodiment of the invention, a plurality of beam masks is provided at predetermined positions relative to the ROI. In this case, the beam masks are called frame masks. The beam masks are distributed around the ROI. In this case, the projection directions can be selected by driving at least one energy input beam source at each of the frame masks. As an example, a plurality of energy input beam sources can be distributed according to the distribution of the beam masks. Alternatively, one energy input beam source is serially moved to each of the beam masks.

For an adaptation to discrete reconstruction algorithms, the energy input beam components are formed with an equal angle spacing. The projection lines passing the through holes of the mask source cross a spherical surface around the source with equal arc length spacing. To this end, the beam mask can have a planar shape or a curved shape (e.g. cylindrical shape). If according to a particularly preferred embodiment of the invention a planar beam mask is used with through holes all having an equal size or a curved beam mask is used with through holes having different sizes, a complete irradiation of the region of investigation without overlap of the energy input beam components being parallel to a particular projection direction can be obtained. In this case, artifacts can be reduced in the image reconstruction. Alternatively, a planar beam mask with through holes all having an equal size or a curved beam mask can be used with through holes having different sizes.

According to a further advantageous embodiment of the invention, the energy input beam is shaped not only with regard to forming the energy input beam components, but also with regard to the outer boundary of the energy input beam. To this end, the imaging method of the invention comprises the further step of setting the beam angle of the energy input beam. This embodiment has particular advantages with regard to an adaptation of the beam source (possibly in combination with the beam mask) to a particular object to be investigated. For irradiating a small object, the beam angle can be decreased so that the overall irradiation dose can be reduced.

Preferably, the beam angle is set with an aperture serving as a diaphragm or shutter. Advantageously, the aperture has a simple construction. Furthermore, it can be simply mounted on a conventional imaging device, like e.g. a conventional CT device for an adaptation to the present invention. Further advantages of the aperture derive from the availability of two degrees of freedom for adjusting the beam angle. With a first alternative, the beam angle is adjusted by setting a diameter of the aperture. This allows a flexible adaptation of the aperture to the object under investigation. According to a second alternative, the beam angle is adjusted by setting a distance between the aperture and the beam source. With the decreasing distance, the beam angle is increased. Both alternatives can be combined.

According to a second general aspect of the invention, an imaging method for imaging the ROI is provided wherein the ROI is irradiated using a method according to the above first general aspect and a plurality of projection functions corresponding to the plurality of projection directions is determined. Each of the projection functions comprises attenuation values measured with energy input beam components being parallel to a current projection direction. The measured attenuation values are subjected to an image reconstruction procedure which is known as such.

The measured attenuation values provide discrete projection profiles representing the projection functions, wherein the projection values of each discrete projection profile comprise the attenuation values corresponding to predetermined energy input beam components with the same projection direction.

The present invention provides another essential advantage in terms of data handling. Due to an adjustment of the cross-sections of the energy input beam components with the beam mask, attenuation values can be measured with predetermined groups of detector elements of the detector device. The groups of detector elements have predetermined, e.g. equal sizes for all beam components. Only these predetermined groups are to be read out without resizing so that the amount of data to be processed is reduced. Preferably, the attenuation values are measured with at least one 1-dimensional straight detector or with at least one 2-dimensional planar detector.

Advantageously, the imaging method of the invention can be implemented with various image reconstruction procedures. Preferably, an image reconstruction procedure is used as described in EP 04031043.5, the priority of which is claimed with the present specification. With this method, the image function is determined from Radon data comprising a plurality of projection functions measured corresponding to the plurality of predetermined projection directions. The image function is determined as a sum of polynomials multiplied with values of the projection functions. In practical implementations, this image reconstruction is based on the measurement of attenuation values corresponding to the discrete irradiation beam components having equal angles relative to each other. Alternatively, the image reconstruction procedure can comprise a decomposition of the attenuation values as described with further details by T. Bortfeld et al. (see above).

It is an essential advantage of the invention, that the imaging can be used in various applications like many applications in medical imaging, for example CT, PET, SPECT, etc. However, there are a lot more possible applications like light tomography, any multidimensional imaging for industrial testing or biological research and so on. Preferably, the image function is determined from Radon data measured in an X-ray computer tomography (CT) device, a PET imaging device, a SPECT imaging device, or a neutron based transmission detection system. The object under investigation comprises e.g. a biological organism or a part thereof, a fluid composition, a solid material, a work-piece, and/or an object to be investigated for security reasons.

According to a third general aspect of the invention, an imaging device for imaging a region of investigation of an object is provided, wherein the imaging device includes at least one beam mask made of an energy input shielding material with through holes. The beam mask is adapted for forming individual, discrete energy input beam components. Furthermore, the imaging device comprises a measuring device for measuring projection functions corresponding to a plurality of projection directions. The measuring device includes at least one energy input beam source and at least one detector device for measuring the projection functions. The energy input beam source is arranged for creating at least one energy input beam to be shaped with the beam mask. Furthermore, the imaging device includes a reconstruction circuit for reconstructing an image function on the basis of measured projection functions.

Preferably, the energy input beam source being a adapted for creating a fan beam or a cone beam source is movably arranged on a source carrier. Particularly preferred is a source carrier which has a ring shape so that the energy input beam source can be rotated e.g. on a circle or along a helical path around the object.

The detector device comprises at least one detector array of detector elements for detecting attenuation values representing the attenuation of the energy input corresponding to the plurality of predetermined projection directions.

According to further preferred embodiments of the invention, the imaging device comprises at least one of a first adjustment device for adjusting a distance between the source mask and the energy input beam source and a second adjustment device for adjusting a diameter of an beam angle aperture and/or a distance between the aperture and the energy input beam source.

If the at least one beam mask comprises one source mask being movable with the energy input beam source, in particular with the fan or cone beam source, advantages with regard to the adjustment of the source relative to the mask can be obtained. Preferably, the source mask is detachably connected with the energy input beam source, so that the imaging device can be adapted to a particular application simply by changing the source mask.

If a plurality of frame masks for shaping the energy distribution function of the energy input beam source is provided as beam mask(s), advantages with regard to setting the projections directions can be obtained. Preferably, the frame masks are fixed at equal arc lengths on a common source carrier. As an example, the source carrier is a ring-shaped shield containing the frame masks. Advantageously, the energy input beam source can be shielded with the ring-shaped shield at positions other than the positions of the frame masks. Accordingly, an essential dose reduction can be obtained.

According to a further modification of the invention using the frame masks, the detector device comprises a plurality of fixed frame detectors for detecting attenuation values representing the attenuation of energy input corresponding to the plurality of predetermined projection directions. In this case, the frame detectors can be fixed on the source carrier at predetermined positions. Preferably, the frame detectors are positioned adjacent to the frame masks.

According to various preferred applications of the invention, the measuring device comprises an X-ray computer tomography (CT) device, an ultrasound tomography device, a PET imaging device, a light tomography device, a Gamma-ray imaging device, a SPECT imaging device, or a neutron based transmission detection system.

According to a fourth general aspect of the invention, a beam mask is provided, which is made of an energy input shielding material with through holes. The energy input shielding material comprises e.g. tungsten, lead or copper. Tungsten is preferred in terms of a high absorption (shielding effect) and high mechanical stability. The beam mask is capable of forming energy input beam components for irradiating a region of investigation of an object.

BRIEF DESCRIPTION OF THE DRAWINGS

Further details and advantages of the invention are described in the following with reference to the attached drawings, which show.

EMBODIMENTS OF THE INVENTION

The invention is described in the following with reference to the application in computer tomography. In this case, the imaging device according to the invention includes the main components of a current medical CT-system, with the energy input beam being an X-ray beam. It is emphasized that the invention can be implemented in an analogous way with the other applications mentioned above. Furthermore, the following description of the preferred embodiments mainly refers to the step of energy beam shaping with a beam mask. Details of CT or other imaging devices as well as details of the image reconstruction used for implementing the invention are not described as they are known from conventional techniques or from EP 04031043.5.

Figure 1:
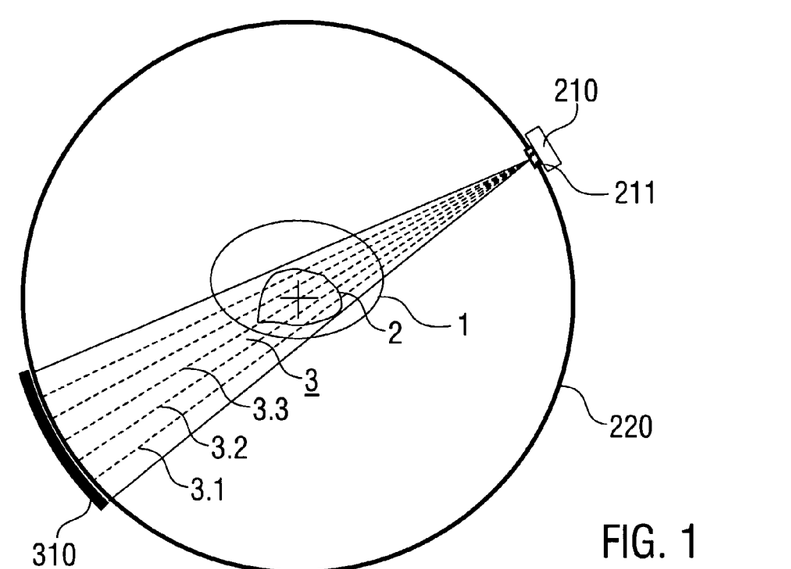
FIG. 1 a schematic illustration of an embodiment of beam shaping according to the invention.

Directing a discretized fan or cone beam 3 through an object 1 with ROI 2 in a CT system for collecting projection data is schematically illustrated in FIG. 1. The CT-system (not completely illustrated, for further components see FIG. 8) includes a ring-shaped source carrier 220 (CT ring) in which the radiation source 210 (X-ray tube) and a detector device 310 are rotating in a way that the whole system can finish a complete turn within e.g. 0.3 to 0.5 s.

As a beam mask, the source mask 211 is used, which is detachably fixed to the radiation source 210. The source mask 211 is adapted for shaping the energy distribution function of the radiation source 210. To this end, the source mask 211 is made of an energy input shielding material with through holes. Discrete, individual X-ray beam components 3.1, 3.2, 3.3, . . . passing the through holes are formed for the above image reconstruction methods, which do not require all possible ray components resulting from the geometry of the tube and the detector geometry for the reconstruction.

The fan beam 3 is directed with varying projection directions through the ROI 2. The projection directions are adjusted in a way that a predetermined number of parallel X-ray beam components is achieved for the imaging conditions. Each fan beam 3 represents a bundle of fan beam components 3.1. 3.2, 3.3 . . . Each of the fan beam components 3.1. 3.2, 3.3 . . . can be considered as a straight pencil beam. While these pencil beams of one fan beam do not have the same individual projection directions, the determination of discrete projection profiles for image reconstruction is obtained by resorting beam components, which belong to different projections directions of the beam 3. As the result, groups of parallel beam components are obtained.

The detector device 310 is a linear or 2-dimensional array of detector elements being shaped according to a spherical reference surface adapted to the radius of the CT ring. Alternatively, a detector device with a straight (1-dimensional) or a planar (2-dimensional) arrangement of detector elements can be used. The detector device 310 consists of e.g. 1 to 64 rows of detector elements (if it is more than one row it would be called a multi-slice-CT) and approximately 700 and 1000 detector elements per row. Current detector elements have a size of e.g. 0.5 to 1.0 mm. Within each single turn the data are read about 1000 times. The object 1, e.g. a patient, is moving through the CT-ring by using a patient table, that is moving continuously. By this method a so-called helical or spiral CT data set can be gathered, because the data that are collected are located on a spiral net.

Further details of various source masks used according to the invention are shown in FIGS. 2 to 5. The source mask 211 comprises a shielding plate 212 for example made by tungsten with through holes 213. The source mask is fixed to the radiation source (e.g. X-ray tube), in particular to a frame 214 of an output window 215 of the radiation source 210 by a detachable fixing element, like e.g. a clip element or a snap connection.

The shielding plate 212 can have a cylindrical shape (FIGS. 2, 4) or a planar shape (FIGS. 3, 5) or any other appropriate shape adapted to the geometric conditions of the imaging device. A cylindrical shielding plate 212 is oriented with the cylinder axis parallel to the axis of a CT ring. The thickness of the shielding plate 212 is e.g. 100 μm to 5 mm. The through holes 213 are arranged such that the projection lines starting at the radiation source 210 cross the circle in line with the detector elements at predetermined positions, in particular, they can be arranged with an equal arc length spacing. Depending on the imaging conditions, the through holes 213 are arranged with a line or an area distribution.

The number and size(s) of the through holes 213 is selected in dependence on the particular application of the imaging method. For CT imaging, e.g. 200 through holes 213 are provided on an area in the range of about 1 mm² to 100 mm². Accordingly, the discrete fan beam 3 comprises e.g. 200 straight fan beam components. By increasing the number of rays and projections, a higher resolution can be achieved, that means the number of pixels which can be reconstructed free of artifacts can be increased.

Figure 2:
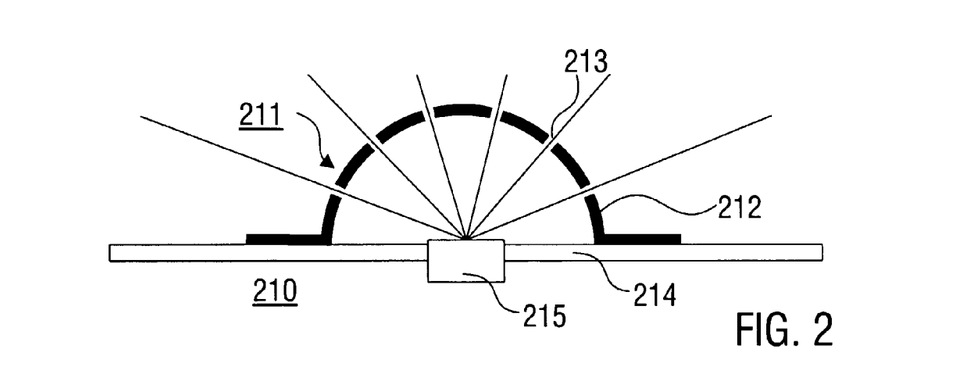
FIGS. 2 to 5 schematic illustrations of embodiments of beam masks used according to the invention.
Figure 3:
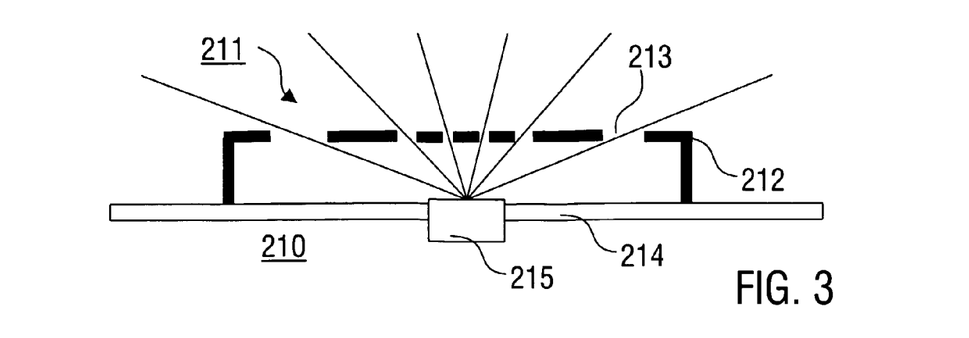
Figure 4:
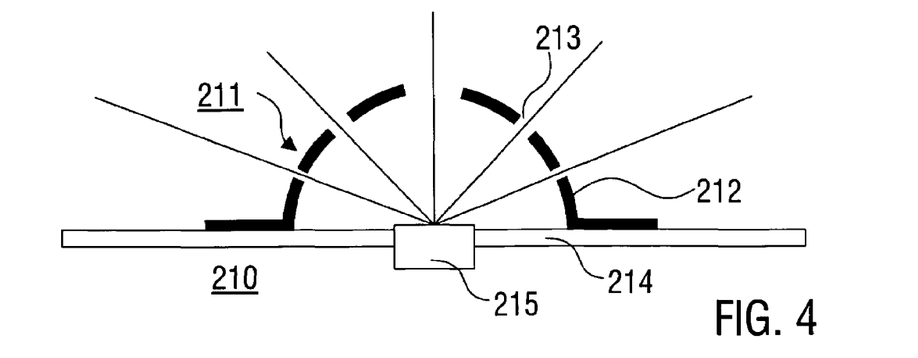
Figure 5:
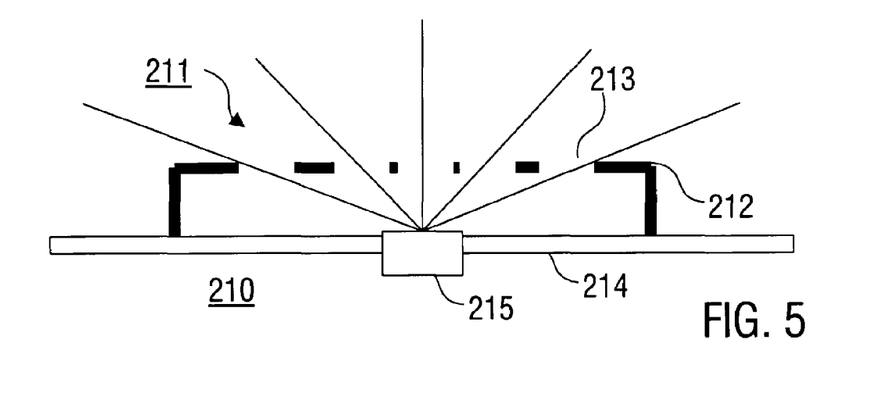

According to FIGS. 2 and 3, the sizes of the through holes 213 are selected such, that all beam components have the same cross-section, i.e. all through holes of the cylindrical mask have the same size (e.g. 10 to 200 μm) while through holes in the centre of the planar source mask beam 211 are smaller than through holes at the outer boundary of the planar source mask beam 211. On the other hand, according to FIGS. 4 and 5, the sizes of the through holes 213 are selected such, that the beam components have varying cross-sections in the detector domain. Preferably, the cross-sections are selected in the range of e.g. 100 μm to 4 mm. In particular, the cross-sections are set in dependence on the detector resolution, which can be obtained with a particular detector. The largest cross-sections are provided in the centre of beam 3, while the smallest cross-sections are provided at the boundary of beam 3.

Figure 6:
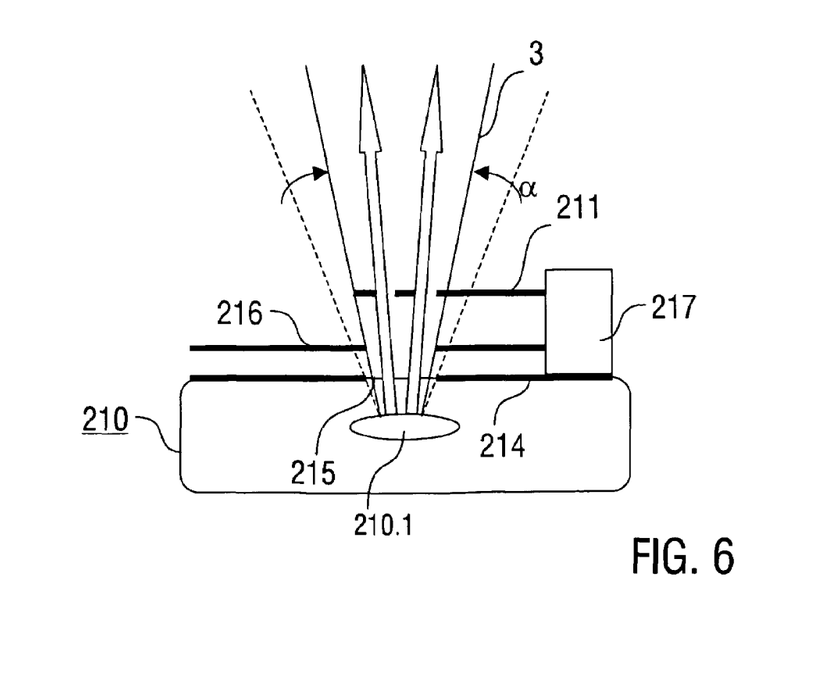
FIG. 6 a schematic illustration of the combination of a beam source with a beam angle aperture and a source mask according to the invention.

FIG. 6 schematically shows an embodiment of combining the radiation source 210 with the source mask 211 and a beam angle aperture 216. An adjustable carrier 217 is arranged on the frame 214 of the output window 215 for holding at least one of the components 211 and 216. Generally, the adjustable carrier 217 serves as at least one adjustment device. The beam angle aperture 216 is made of a shielding plate with a central hole. The diameter and/or the perpendicular distance between the beam angle aperture 216 and the radiation emitter 210.1 of the radiation source 210 can be adjusted with the adjustable carrier 217 for defining a beam angle α of the fan beam 3. The source mask 211 is shaped as outlined above for defining the beam components. The distance between the source mask 211 and a radiation emitter 210.1 can be varied for obtaining a required imaging resolution. The adjustable carrier 217 can be operated manually or electrically, e.g. with piezo-electric drive units.

With the discrete fan beam 3 generated by the mask illustrated above, the signals from the detector elements of the detector device detecting the attenuation along the corresponding projection lines are read-out at certain positions of the radiation source and the detector device only. The read out positions are those arc length positions on the ring-shaped source carrier, which fulfil the condition of selecting parallel fan beam components with the same projection directions.

For reducing the radiation or particle exposure of the object under investigation, it is preferred to direct the energy input (e.g. radiation) into the object under investigation only at the above read-out positions, namely the detector element signals are read out only when the combination of a radiation source and the detector device is oriented to the suitable positions. During the movement of the radiation source, this condition is fulfilled for certain times and/or for certain arc length positions of the radiation source. As long as the read-out condition is not fulfilled, the radiation source can be shut off or shielded. Shielding the radiation source is preferred for keeping radiation conditions stable.

Figure 7:
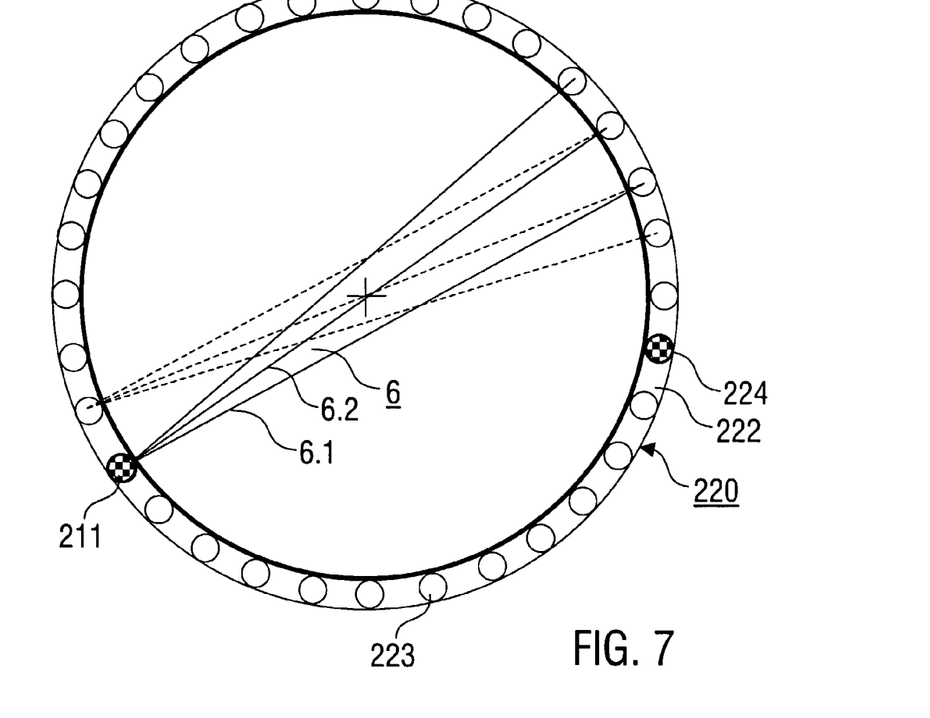
FIG. 7 a further illustration of directing discretized fan beams through an object under investigation.

The shielding function can be fulfilled by a ring-shaped shield 222 which is schematically illustrated in FIG. 7 with a plurality of radiation windows 223. The ring-shaped shield 222 can be detachably fixed to the source carrier 220 for adapting the geometric properties of the shield 222 to the practical application and in particular to the mask used. As an example, the ring-shaped shield 222 comprises 201 radiation windows 223 each having a diameter of 6 mm (with a diameter of the CT-ring: 80 cm).

Figure 8:
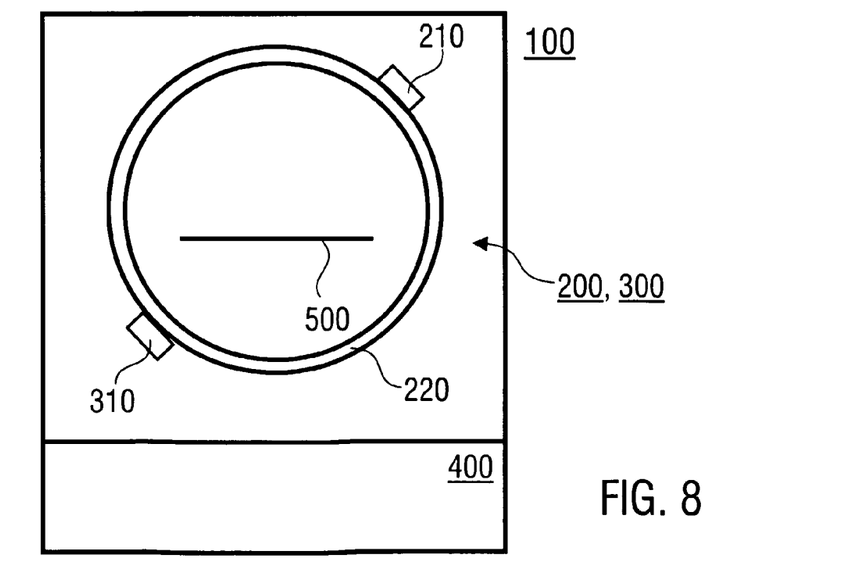
FIG. 8 a schematic representation of an embodiment of an imaging device according to the invention.

The source masks 211 described above can be omitted if each radiation window 223 of the ring-shaped shield 222 is provided with a frame mask 224 which is illustrated in FIG. 7 as an example only. In fact, the source and frame masks 211, 224 need not be provided simultaneously. The frame masks 224 can be designed as the source masks shown in FIGS. 2 to 5. FIG. 8 schematically illustrates an embodiment of the imaging device 100. The imaging device 100 comprises the measuring device with an energy generator 200 and a detector device 300 and the reconstruction device 400 being connected with the measuring device 200, 300. Furthermore, a holding device 500 is provided, which is e.g. a carrier table as it is known from CT systems or any other carrier or substrate holder for arranging an object under investigation in the measuring device and for adjusting the geometry of the object relative to the energy generator 200 and the detector device 300. Further components like a control device, a display device etc. (not shown) are provided for as they are known per se from prior art devices.

The energy generator 200 comprises the radiation source 210, like e.g. a movable X-ray tube with a source mask arranged on the source carrier 220 (e.g. a guide rail or gantry). The detector device comprises a detector array 310 which is movably arranged on the source carrier 220 in opposite relationship relative to the radiation source 210. With this structure, the projection direction through the ROI (parallel to the plane of drawing) can be set by rotating the combination of components 210, 310 around the holding device 500.

The source carrier 220 is illustrated as a circle allowing a rotation of the energy generator 200 and the detector device 300 around an object. According to a modification, the source carrier can have an ellipse shape or another shape. This can represent an advantage in terms of an adaptation to the geometry of the object to be investigated.

The invention claimed is:

1. A method, comprising:
   generating at least one energy input beam with at least one energy input beam source;
   forming a plurality of energy input beam components from the at least one energy input beam by directing at least a portion of the energy input beam to an energy input shielding beam mask that includes a plurality of apertures, wherein all energy input beam components have the same cross-section; and
   irradiating a region of investigation (ROI) with the energy input beam components along a plurality of projection directions.

2. The method claim 1, further comprising:
   securing the beam mask with respect to the at least one energy input beam source; and
   moving the at least one energy input beam source and the beam mask relative to the ROI to irradiate the ROI along the plurality of projection directions.

3. The method of claim 1, wherein the plurality of energy input beam components are formed by directing at least a portion of the energy input beam to a plurality of energy input shielding beam masks, and further comprising:
   situating each of the plurality of beam masks at respective fixed positions relative to the ROI; and
   operating the at least one energy input beam source at each of the fixed positions of the beam masks so as to irradiate the ROI along the plurality of projection directions.

4. The method of claim 1, wherein the beam mask is substantially planar and the apertures in the beam mask have different sizes.

5. The method of claim 1, wherein the beam mask is curved and the sizes of the apertures are substantially equal.

6. The method of claim 1, further comprising selecting propagation directions of the energy input beam components by adjusting a distance between the energy input shielding beam mask and the at least one energy input beam source.

7. The method of claim 1, further comprising selecting an energy input beam angular aperture.

8. The method of claim 7, wherein the energy input beam angular aperture is selected by directing the energy input beam to a beam angle adjustment aperture.

9. The method of claim 8, wherein the energy input beam angular aperture is selected by selecting a diameter of the beam angle adjustment aperture and a distance between the beam angle adjustment aperture and the at least one energy input beam source.

10. The method of claim 1, further comprising:
    determining a plurality of projection functions corresponding to the plurality of projection directions, wherein each projection function includes attenuation values associated with energy input beam components that are substantially parallel; and
    reconstructing an image based on the attenuation values.

11. The method of claim 1, further comprising:
    obtaining attenuation values at predetermined read-out positions;
    determining a plurality of projection functions based on the obtained attenuation values; and
    reconstructing an image based on the attenuation values.

12. The method of claim 10, further comprising measuring the attenuation values with a detector device comprising a plurality of detector elements, wherein the attenuation values are obtained from predetermined groups of the detector elements.

13. The method of claim 10, wherein image reconstruction comprises determining an image function as a sum of polynomials multiplied by values based on the projection functions.

14. The method of claim 10, wherein image reconstruction comprises decomposing the attenuation values subject to a filtered back-projection reconstruction.

15. The method of claim 10, wherein the attenuation values correspond to measured Radon data.

16. The method of claim 10, wherein the at least one energy input beam source produces an energy input beam selected from the group consisting of an X-ray beam, a positron beam, an optical beam, a neutron beam, and a gamma ray beam.

17. An apparatus, comprising:
    at least one energy input beam source configured to generate at least one energy input beam;
    at least one energy input shielding beam mask having a plurality of apertures configured to form a plurality of energy input beam components, wherein the sizes of the apertures are selected such that all beam components have the same cross-section and the energy input shielding beam mask is situated to direct the energy input beam components to an object; and
    a radiation detection system configured to measure projection functions associated with the object based on the energy beam components directed to the object and corresponding to a plurality of projection directions.

18. The apparatus of claim 17, wherein the energy input shielding beam mask is substantially planar and the apertures in the beam mask have different sizes.

19. The apparatus of claim 17, wherein the energy input shielding beam mask is curved and the sizes of the apertures are substantially equal.

20. The apparatus of claim 17, wherein the energy input shielding beam mask is substantially planar and the apertures are substantially a common size.

21. The apparatus of claim 17, wherein the energy input shielding beam mask is curved and the apertures have different sizes.

22. The apparatus of claim 17, further comprising an adjustment device configured to adjust a distance between the energy input shielding beam mask and the at least one energy input beam source.

23. The apparatus of claim 17, wherein the at least one energy input beam source is movable relative to the object.

24. The apparatus of claim 17, wherein the energy input shielding beam mask includes a source mask movable with the at least one energy input beam source.

25. The apparatus of claim 17, wherein the source mask is removable from the at least one energy input beam source.

26. The apparatus of claim 17, wherein the energy input shielding beam mask includes a plurality of frame masks configured to shape an energy distribution produced by the at least one energy input beam source, and further comprising a source carrier to which the frame masks are fixed at predetermined mask positions.

27. The apparatus of claim 26, wherein the predetermined mask positions are spaced by substantially equal arc lengths with respect to the object.

28. The apparatus of claim 27, wherein the source carrier comprises a cylindrical shield configured to shield the object from the at least one energy input beam source with the energy input beam source situated at positions other than the predetermined positions.

29. The apparatus of claim 26, wherein the radiation detection system includes a plurality of frame sensors fixed on the source carrier at predetermined sensor positions and situated to detect attenuation values corresponding to the plurality of projection directions.

30. The apparatus of claim 17, wherein the at least one energy input beam source is configured to produce an energy input beam selected from the group consisting of an X-ray beam, a positron beam, an optical beam, a neutron beam, and a gamma ray beam.

* * * * *